US008753656B2

(12) United States Patent
Stamets

(10) Patent No.: US 8,753,656 B2
(45) Date of Patent: Jun. 17, 2014

(54) CONTROLLING ZOONOTIC DISEASE VECTORS FROM INSECTS AND ARTHROPODS USING PRECONIDIAL MYCELIUM AND EXTRACTS OF PRECONIDIAL MYCELIUM FROM ENTOMOPATHOGENIC FUNGI

(76) Inventor: Paul Stamets, Shelton, WA (US)

( * ) Notice: Subject to any disclaimer, the term of this patent is extended or adjusted under 35 U.S.C. 154(b) by 0 days.

(21) Appl. No.: 13/317,613

(22) Filed: Oct. 24, 2011

(65) Prior Publication Data
US 2012/0039976 A1 Feb. 16, 2012

Related U.S. Application Data

(60) Continuation-in-part of application No. 13/066,566, filed on Apr. 18, 2011, now Pat. No. 8,501,207, which is a division of application No. 12/288,535, filed on Oct. 20, 2008, now Pat. No. 7,951,389, which is a division of application No. 10/853,059, filed on May 24, 2004, now abandoned, which is a division of application No. 09/969,456, filed on Oct. 1, 2001, now Pat. No. 7,122,176, which is a continuation-in-part of application No. 09/678,141, filed on Oct. 4, 2000, now Pat. No. 6,660,290, application No. 13/317,613, which is a continuation-in-part of application No. 12/284,646, filed on Sep. 24, 2008, which is a continuation-in-part of application No. 11/728,613, filed on Mar. 27, 2007, now abandoned, which is a continuation-in-part of application No. 11/386,402, filed on Mar. 22, 2006, now abandoned, which is a continuation-in-part of application No. 11/145,679, filed on Jun. 6, 2005, now abandoned, which is a continuation-in-part of application No. 11/029,861, filed on Jan. 4, 2005, now abandoned.

(60) Provisional application No. 60/534,776, filed on Jan. 6, 2004, provisional application No. 60/994,972, filed on Sep. 24, 2007.

(51) Int. Cl.
A01N 25/32 (2006.01)
A01N 65/00 (2009.01)
A01N 25/00 (2006.01)
A01N 25/02 (2006.01)

(52) U.S. Cl.
CPC .............. *A01N 25/32* (2013.01); *A01N 25/006* (2013.01); *A01N 25/02* (2013.01); *A01N 65/00* (2013.01)
USPC ..................... 424/406; 424/93.5; 424/195.15; 424/405; 424/409

(58) Field of Classification Search
CPC ...................................................... A01N 65/00
USPC ................................... 424/84, 404–420, 93.5
See application file for complete search history.

(56) References Cited

U.S. PATENT DOCUMENTS

| 5,360,607 | A  | * | 11/1994 | Eyal et al. | ..................... 424/93.5 |
| 5,888,989 | A  | * | 3/1999  | Kern    | ................................ 514/63 |
| 2004/0211721 | A1 | * | 10/2004 | Stamets | ........................ 210/601 |
| 2005/0176583 | A1 | * | 8/2005  | Stamets | ........................ 504/100 |

OTHER PUBLICATIONS

Sampson—Atlas of Entomopathogenic Fungi—1988 pp. IX.*

* cited by examiner

*Primary Examiner* — Neil Levy
(74) *Attorney, Agent, or Firm* — William R. Hyde

(57) ABSTRACT

The present invention utilizes extracts of the pre-sporulation (preconidial) mycelial stage of entomopathogenic fungi as insect and arthropod attractants and/or pathogens and can be employed to limit the zoonotic diseases they transmit. The fungus can be cultivated on grain, wood, agricultural wastes or other cellulosic material and extracts can be made thereof. More than one fungus and substrate can be used in combination with one or more antimicrobial, antiprotozoal, antiviral, and genetically modified agents that result in reduced spread of contagions and lessens the damage they inflict on animals, and plants.

6 Claims, No Drawings ating
CONTROLLING ZOONOTIC DISEASE VECTORS FROM INSECTS AND ARTHROPODS USING PRECONIDIAL MYCELIUM AND EXTRACTS OF PRECONIDIAL MYCELIUM FROM ENTOMOPATHOGENIC FUNGI This application is a continuation-in-part of U.S. patent application Ser. No. 13/066,566, filed Apr. 18, 2011, currently co-pending, which is a divisional of U.S. patent application Ser. No. 12/288,535, filed Oct. 20, 2008 (now issued as U.S. Pat. No. 7,951,389), which is a divisional of U.S. patent application Ser. No. 10/853,059, filed May 24, 2004, which is a divisional of U.S. patent application Ser. No. 09/969,456, filed Oct. 1, 2001 (now issued as U.S. Pat. No. 7,122,176), which is a continuation-in-part of U.S. patent application Ser. No. 09/678,141, filed Oct. 4, 2000 (now issued as U.S. Pat. No. 6,660,290). This application is also a continuation-in-part of U.S. patent application Ser. No. 12/284,646, filed Sep. 24, 2008, currently co-pending, which claims the benefit of U.S. provisional patent application Ser. No. 60/994,972, filed Sep. 24, 2007 and which is a continuation-in-part of U.S. patent application Ser. No. 11/728,613, filed Mar. 27, 2007, which is a continuation-in-part of U.S. patent application Ser. No. 11/386,402, filed Mar. 22, 2006, which is a continuation-in-part of U.S. patent application Ser. No. 11/145,679, filed Jun. 6, 2005, which is a continuation-in-part of U.S. patent application Ser. No. 11/029,681, filed Jul. 4, 2005, which claims the benefit of U.S. provisional patent application Ser. No. 60/534,776, filed Jan. 6, 2004, all of which are incorporated herein by reference.

BACKGROUND OF THE INVENTION

1. Field of the Invention

The present invention relates to mycology, entomology, and the use of preconidial preparations of entomopathogenic fungi as attractants (mycoattractants) and biopesticides (mycopesticides, mycoinsecticides) in combination with other technologies to control, decrease, limit or prevent the spread of diseases carried by insects and/or other arthropods. More particularly, the invention relates to the control of zoonotic diseases by attracting, and attracting and killing insects, including ants, flies, beetles, cockroaches, bed bugs, mosquitoes, grasshoppers and other arthropods such as ticks, mites, midges, lice and fleas, using pre-sporulating mycelia of entomopathogenic fungi and extracts of pre-sporulating mycelia.

2. Description of the Related Art

Diseases emanating from ecologically distressed and polluted environments increasingly threaten animals and plants. With deforestation, habitat destruction, decline in water quality, decreases in biodiversity, all of which are exacerbated by global climate change and human impacts, zoonotic diseases are increasingly a threat to healthy environments and their inhabitants, especially animal populations, including humans and their livestock. Many of these disease-causing organisms are carried by or bred within insects or other arthropods. Insects are any of the large class (Insecta) of small arthropod animals characterized, in the adult state, by division of the body into head, thorax, and abdomen, three pairs of legs on the thorax, and, usually, two pairs of membranous wings; arthropods are any of the largest phylum (Arthropoda) of invertebrate animals with jointed legs, a segmented body, and an exoskeleton, including herein insects, arachnids such as spiders, mites and ticks, and myriapods. Since many of these bite humans and livestock, as well as damage plants, they transmit a wide variety of diseases, many of which result in billions of dollars worth of damage to economies worldwide.

Insects are among the most diverse and numerous life forms on earth. While the majority of the one million named species of insects are considered beneficial, somewhere from 1% to 5% are considered to be pests. Some of these insect pests not only cause tremendous losses in terms of direct destruction of crops, livestock, and human dwellings, they are also vectors for pathogens including protozoa, round worms, bacteria, and viruses that cause devastating human health problems. As climates change, with an overall tendency to warming, tropical and subtropical diseases are spreading into temperate regions, once devoid of these threats. The negative physical, mental, economic, social, and ecological implications of disease carrying pest insects and arthropods are difficult to quantify since their effects are wide-ranging and multidimensional. As ecosystems in which humans dwell are harmed, water is polluted, sanitation hurdles mount, toxins are accumulated, and food scarcity increases, animals (including humans) become much more susceptible to infection from pathogen-carrying insects and arthropods as their innate immune systems are weakened. Chemical pesticides, antibiotics, and vaccinations are notoriously ineffective against long-term exposure to populations of rapidly evolving organisms. Additionally, resistance to pesticides and antimicrobials can result in "super-bugs" which often develop in both insects and the microbes they transmit. As diseases ebb and flow, we need a more sophisticated way of out-smarting the vectors that carry them. If the vector can be stopped, the disease can be stopped. By using attractants from entomopathogenic fungi, this new approach allows the unusual flexibility of being able to switch or combine attractant extracts and mycelium sourced by tapping into the vast and continually evolving genome of naturally occurring wild or human-improved strains.

Many insects and arthropods are vectors for contagions. Some in particular are common carriers of pathogens and contagions. Many of these contagions are spread by simple contact, some are spread from bites or proboscis punctures, while others can be transmitted to animals when they consume these disease-laden insects.

Zoonotic disease is defined as any disease that is spread from animals to people. Any subsequent insect controlling technology can be enhanced since the insects and arthropods become concentrated as a result of the attractant properties of the preconidial mycelium or extract of selected entomopathogenic fungi. The further novelty of this invention is that it allows other technologies that limit disease to work more effectively by concentrating and localizing the disease-spreading organism to a more centralized locus, reducing expenses while enhancing efficacies. In essence, disease vectors by insects and arthropods can be better controlled.

Ants can carry diverse populations of pathogenic bacteria. For instance, Pharaoh ants (*Monomorium pharaonis* and related species) are known as vectors to more than dozen pathogenic bacteria, including *Salmonella* spp., *Staphylococcus* spp., and *Streptococcus* spp., and are especially dangerous to burn victims recovering in hospital environments. See Beatson S. H., "Pharaoh ants as pathogen vectors in hospitals," *Lancet* 1: pp. 425-427(1972); Haack K. D., Granovsky T. A., Ants, In *Handbook of Pest Control*, Story K. and Moreland D. (eds.), Franzak & Foster Co., Cleveland, Ohio. pp. 415-479 (1990); and Smith E. H., Whitman R. C., *Field Guide to Structural Pests*, National Pest Management Association, Dunn Loring, Va., (1992).

Although we have identified many diseases mosquitoes carry, we are unlikely to have identified them all. More mosquito-pathogen vectors are likely to be discovered as insects (and arthropods) evolve and species populations re-mix. We know that mosquitoes can be the vector for viruses, using their proboscis as a form of a syringe capable for injecting many viruses, specifically West Nile virus, encephalitis viruses (Western equine encephalitis, St. Louis encephalitis, La Crosse encephalitis, Japanese encephalitis, Eastern equine encephalitis), Yellow Fever, and Dengue Fever. How many other viruses carried by mosquitoes, yet unknown or not yet evolved, will be discovered? Surely, there will be more.

Mosquitoes also inject protozoa into humans, including malaria (*Plasmodium falciparum*), which still results in millions of deaths per year worldwide. Control measures have included the use of chemical pesticides such as DDT™ and Deltamethrin™; however, their recurrent and prolonged use stimulates resistance. It seems Nature always finds a way around chemical "solutions." To resolve complex problems in Nature, complex solutions are needed. This invention speaks directly to this issue.

Even the use of pesticide impregnated mosquito nets, which have been initially effective at reducing malaria infection, are not a long-term solution. Paradoxically a new study published in the prestigious medical journal *The Lancet*, indicates that human populations become more susceptible to malarial diseases by limiting their exposure to bites from mosquitoes. The research team, led by Dr. Jean-Francois Trape of the Institut de Recherche pour le Developpement in Dakar, found that malaria infection rates in certain segments of the population rose to levels higher than before the introduction of bed nets. The researchers collected specimens of *Anopheles gambiae*, the mosquito species responsible for transmitting malaria to humans in Africa. Between 2007 and 2010 the proportion of the insects with a genetic resistance to one type of pesticide rose from 8% to 48%. By 2010, the proportion of mosquitoes resistant to Deltamethrin, the chemical recommended by the World Health Organization for bed nets, was 37%. In the last four months of the study, the researchers found that the incidence of malaria attacks returned to high levels. Among older children and adults the rate was even higher than before the introduction of the nets. The researchers argue that the initial effectiveness of the bed nets reduced the amount of immunity that people acquire through exposure to mosquito bites. Combined with resurgence in resistant insects, there was a rapid rebound in infection rates. The authors are worried that their study has implications beyond Senegal, writing "these findings are a great concern since they support the idea that insecticide resistance might not permit a substantial decrease in malaria morbidity in many parts of Africa." Trape, J-F. et al., "Malaria morbidity and pyrethroid resistance after the introduction of insecticide-treated bednets and artemisinin-based combination therapies: a longitudinal study," *The Lancet Infectious Diseases*, early online publication, doi: 10.1016/S1473-3099(11)70194-3 (2011).

Below is a short summary of insects and arthropods with some of the zoonotic pathogens they transmit.

Insects and Arthropods Vectoring Zoonotic Pathogens

Ants: Bacteria (*Salmonella* spp., *Staphylococcus* spp., *Streptococcus* spp., etc.) Example: Fire ants spread several bacterial diseases in hospitals, including *Staphylococcus*, *Salmonella* and *Clostridium*.

Mosquitoes: Malaria protozoa (*Plasmodium falciparum*) carried by 30-40 species, including *Anopheles gambiae*. Viruses: West Nile (carried by more than 42 species), encephalitis, Yellow Fever and Dengue Fever (carried by several species of *Aedes*, including *A. aegypti*).

Flies: Bacteria, protozoa (ex. Tsetse fly carries the protozoan *Trypanosoma* causing often-fatal 'sleeping sickness'). Flies also spread viruses, including influenza strains H5N2 & H5N1 (bird flu) and H1N1 (swine flu), which can also be carried by Blow Flies (Calliphoridae, *Calliphora vicina* and related species) and the common house fly (*Musca domestica* and related species). Houseflies can also transmit typhoid (*Salmonella typhi*) and dysentery (a disease complex caused by viruses, bacteria, protozoa and parasitic worms). White flies can transmit begomoviruses (family Geminiviridae), criniviruses, ipomoviruses, torradoviruses, and some carlaviruses.

Bed Bugs: MRSA (methicillin resistant *Staphylococcus aureus* bacteria) carried by *Cimex* species. Other bacteria can be transmitted by bed bugs.

Lice and ticks: Bacteria: *Rickettsia* spp. causing Rocky Mountain Spotted fever; *Bartonella vinsonii* & *B. henseiae* causing intramuscular infections; and *Borrelia burgdorferi* causing Lyme disease.

Fleas: Bacteria, including *Yernsia pestis* causing bubonic plague.

Midges: Viruses (Blue tongue virus to cattle, epizootic hemorrhagic disease).

Leafhoppers: Tomato/Tobacco Mosaic viruses, wheat striate mosaic virus, maize fine streak virus, chickpea chlorotic dwarf virus, green petal virus, and others.

Virtually all biting insects and arthropods can result in bacterial or viral infections, either directly from a contagion reservoir within them or from wound exposure to the open environment. This is true with regard to both animal and plant diseases.

The present invention affords yet another new option for disease control: to attract but not necessarily kill mosquitoes, whilst reducing or eliminating their pathogen payloads. This option is important especially in areas where the insect populations are helpful in maintaining biological diversity of other animals that are dependent upon them for food. Removing all the insects from an ecosystem would likely result in unforeseen consequences, beyond that which is readily obvious. The food web is interconnected, and while most experts will agree that reducing disease vectors is prudent; destroying a native insect population is not.

Moreover, since *Metarhizium* species are natural parasites of mosquitoes, the natural genome of this and other entomopathogenic fungi offer sources of ever-evolving libraries of new strains, making resistance much more unlikely compared to chemical pesticides. An additional advantage of using preconidial entomopathogenic fungi such as *Metarhizium anisopliae* is that native strains of this fungus can be isolated wherever mosquitoes live, meaning that the constant co-evolution of this fungus to overcome resistance factors of the mosquitoes provides us with a unique partnership with nature to constantly adapt native, new strains of this fungus for implementation in controlling mosquitoes. Moreover, if new strains of *Metarhizium anisopliae* are blended with any antimicrobial agent, the insects and the diseases they spread can be further controlled. Should the disease organism being carried by, for instance, a mosquito, develop resistance to an antimicrobial or antiviral drug, then a mixture of more than one drug or remedy can be employed to overcome resistance. Thus, this invention allows for a platform for continually out-smarting resistance by blending technologies and combining antimicrobials—out-racing the ability of insects and pathogens to adapt to either the entomopathogenic fungus or the antimicrobial method employed at the points of contact. Such synergism can have many derivative improvements and are expected by this inventor.

As an example, Artemesinin from *Artemesia* plants, has been found to be effective against malaria. Either pure or less expensive crude, extracts containing Artemesinin can be blended with the preconidial extracts and/or mycelium of *Metarhizium anisopliae*. This combination would both attract mosquitoes and upon ingestion of the blended extract reduce the malarial loads they carry. Similarly, other combinations could include any or a plurality of antimalarial drugs or the crude precursors from which they are derived, including but not limited to: Quinine and related agents, Chloroquine, Amodiaquine, Pyrimethamine, Proguanil, Sulfonamides, Mefloquine, Atovaquone, Primaquine, Halofantrine, Doxycycline, and Clindamycin. Moreover, the water/ethanol extracts of some polypore mushrooms, particularly *Polyporus umbellatus* has shown strong antimalarial activity, although the active ingredients have not yet been identified. Lovy, A., B. Knowles, R. Labbe & L. Nolan, "Activity of edible mushrooms against the growth of human T4 leukemia cancer cells, and *Plasmodium falciparum*," *Journal of Herbs, Spices & Medicinal Plants* vol. 6(4): 49-57 (1999). Additionally, other polypore mushrooms, and Basidiomycetes, are likely to produce antimalarial compounds.

Another example would be to blend the extracts or mycelia of preconidial entomopathogenic fungi with the less expensive antiviral drug precursors, expired antiviral drugs, or drugs such as Abacavir, Aciclovir, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Famciclovir, Fomivirsen, Fosamprenavir, Foscarnet, Fosfonet, Ganciclovir, Ibacitabine, Imunovir, Idoxuridine, Imiquimod, Indinavir, Inosine, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir (Tamiflu®), Peginterferon alfa-2a, Penciclovir, Peramivir, Pleconaril, Podophyllotoxin, Protease inhibitors, Raltegravir, Reverse transcriptase inhibitors, Ribavirin, Rimantadine, Ritonavir, Pyramidine, Saquinavir, Stavudine, Tea tree oil, Tenofovir, Tenofovir disoproxil, Tipranavir, Trifluridine, Trizivir, Tromantadine, Truvada, Valaciclovir (Valtrex®), Valganciclovir, Vicriviroc, Vidarabine, Viramidine, Zalcitabine, Zanamivir (Relenza®), and Zidovudine.

This same principle could also be used to enhance more traditional insect control devices. For example, blends of extracts and preconidial mycelium of entomopathogenic fungi can be used to enhance performance of UV light based insect traps such as BASF's "Vector™" or $CO_2$ emitting suction traps. In essence, any current or future method might well result in greater performance for controlling insects, whether these be mosquitoes, flies or others, by employing extracts and mycelium of preconidial entomopathogenic fungi.

Using preconidial entomopathogenic fungi to develop new or enhance existing insect control measures may also be used to help mitigate diseases spread by flies. Flies such as the blood sucking Tsetse fly carry the protozoan *Trypanosoma* that causes an often fatal "sleeping sickness" in Africa. Blow flies, aka 'blue bottle flies' (*Calliphora nigribarbis* and *Aldrichina graham*) and house flies (*Musca domestica*) have both been found by multiple researchers to harbor and carry bird flu viruses, meaning that poultry farms and slaughter houses represent nexus distribution points for this contagion. See http://www.flutrackers.com/forum/showthread-.php?t=29335. According to the researchers, "more than one-third of the adult *Musca domestica* sampled contained AI [avian influenza] virus particles." Blow flies swarm and breed upon carcasses, including birds, as well as broken eggs and bird feces, and can acquire bird flu viruses. The ever-so-common housefly can carry bird flu viruses, and potentially re-infect chickens and other poultry that eat flies regularly. What has not been reported yet is whether or viruses such as bird flu can be transmitted to humans from infected flies. Given the huge swarms of flies that congregate around dead and diseased animals, this vector seems likely. According to the researchers, "more than one-third of the adult *Musca domestica* sampled contained AI virus particles"(http://www.flutrackers.com/forum/showthread.php?t=29640).

As symptoms of bird flu infection may not be evident for a few days, and yet the animals can be infectious, factory farms, and in particular slaughter houses (where blow flies feed on cadavers and also make contact with living animals) can be a serious, although largely unpublicized threat to public health. Flies infected from contacting poultry infected from bird flu, for example, can be eaten by non-infected birds, thus increasing the probably of disease transmission. Thus the need to attract virus-vectoring flies, and to reduce their pathogen payload is dually important. Note that even if the flies are not caught, but seek out, make contact with, and/or ingest the sweet extracts having antiviral or antimicrobial properties, the benefits incurred are that these insects are then less infectious due to reduced levels of contagions.

Because the purification of antimicrobial and antiviral drugs is typically more much expensive than their crude, or semi-pure precursors, this invention anticipates that less-than-pharmaceutical grade antiviral, antimicrobial, and anti-protozoa medicines can be employed in combination with extracts and the mycelium of pre-conidial entomopathogenic fungi to create a successful treatment in the prevention, mitigation, or curing of contagions transmitted by insects and arthropods. Moreover, the inventor's prior research on the use of polypore mushroom derivatives to combat viruses, which employ a similar method of extraction to the methods described herein for the creation of attractant preconidial entomopathogenic extracts, is yet another application of this novel way of limiting zoonotic contagions.

Other insect arthropods such as lice and ticks can carry *Rickettsia* bacteria causing Rocky Mountain Spotted fever. Fleas can transmit bubonic plague (*Yersinia pestis* bacteria) and ticks can carry Lyme disease (*Borrelia* bacteria) to humans, deer, and other animals. 'Bed bugs' (*Cimex* species from the Cimicidae) have also recently been found to carry drug-resistant staph bacteria (MRSA—methicillin resistant *Staphylococcus aureus*), compounding the challenge faced by hospitals, hotels, dormitories, army barracks, prisons, and other densely populated areas. Denser populations of humans and animals—especially denser populations of immunocompromised humans and animals—increase the probably of infection and re-transmission. Whether the initial infection being transmitted from a biting insect or arthropod is from a bacterium or a virus, co-occurrence of non-insect borne diseases may more readily ensue. The now-lowered immunity of the infected animal population at large may, for instance, make the spread of Ebola, Hanta, bird flu viruses, diphtheria, dysentery, and any contagion more readily spreadable. The resultant consequences of a population's lowered immunity can also degrade the overall population's immunological defenses against cancers. Conversely, those already suffering from cancer, or have compromised immune systems due to other diseases, are more susceptible to infection.

Moreover, insects spread viruses into plants. For instance, caterpillars and grasshoppers spread the Tomato-Tobacco Mosaic Virus. For farmers, there are dual advantages for controlling plant eating insects and the crop destroying diseases they spread. By combining extracts from the polypore mushroom, *Fomes fomentarius*, a source of antiviral agents active against the Tobacco Mosaic Virus with extracts of preconidial mycelium of *Cordyceps* species (well known for infecting caterpillars and grasshoppers), farmers could benefit by both limiting these crop damaging insects and lessening the threat of viruses they spread. This is but one of many examples that will become obvious and are expected manifestations of this over-arching invention.

Hence this inventor sees a two-fold need: to control movement of insects, and to control the pathogenic bio-burden of insects and arthropods that transmit diseases to people, animals, and plants. Combining methods and compositions discussed herein to create discrete ways to attract disease-carrying insects and subsequently killing them and/or reducing their pathogenic payloads will be important for protecting environmental health. In the age of technologies creating genetically modified organisms, potentiating pathogen carrying insects as biological weapons is possible and protection from such threats is sorely needed. Hence, this invention could be important for defense against bioterrorism in its many elaborations.

SUMMARY OF THE INVENTION

In view of the absence of using the preconidial mycelium of entomopathogenic fungal mycelium to attract insects and arthropods that carry contagions and disease, the present invention provides improved insect bio control agents, and methods and compositions of using such agents.

The present invention offers a unique approach to zoonotic disease control by attracting insects or arthropods that contact or ingest "preconidial" mycelium of entomopathogenic fungi (that is, mycelium in a developmental state prior to conidia or spore formation) which is also combined with any pest or disease controlling mechanism, another drug, plant derived medicine, pharmaceutical, hormone disrupter, attenuation gene, bacteriophage, or fungus or fungi possessing antimicrobial or anti-viral properties that results in arresting movements by such insects or arthropod while limiting the populations and pathogenicity of their carrier diseases.

Preconidial mycelium is defined as mycelium lacking spores but existing in a state prior to or without spore formation. The preconidial state and preconidial mycelium may include sclerotia or microsclerotia, compact masses of hyphae that are formed by certain fungi and give rise to new fungal growth or spore-producing structures. Commercial conidial formations of *Metarhizium anisopliae* strive to achieve at least 1,000,000 conidia per gram, and optimally 10,000,000-100,000,000+ per gram. Preconidial mycelium is defined in ranges as preferably having less than 10,000 conidia per gram of myceliated substrate, more preferably less than 1,000, and most preferably less than 100 conidia per gram. The preconidial mycelium is optimally without spores. Preconidial mycelium can be created by selectively culturing non-sporulating sectors from entomopathogenic fungi or by chemical agents that temporarily suppress conidia (spore) formation. See U.S. Pat. No. 7,951,389 and other patents by the present inventor. Either way, conidia formation can be re-activated, either naturally or artificially. Using preconidial preparations, mycelium and extracts in a variety of forms—living, frozen, dried, freeze dried, extracted—offers advantages by attracting insects or other arthropods and concentrating them into a more centralized location. Once concentrated, a variety of technologies can be deployed to trap or kill the insects and other arthropods, and reduce the pathogen payload they harbor.

Such preconidial mycelium of entomopathogenic fungi may be used solely as an attractant (either as an attractant for pest insects or as an attractant for beneficial insects) or as an attractant and pathogen where the preconidial mycelium is both the attractant and the pathogenic agent. Additionally, whence the insects or arthropods make contact with the preconidial entomopathogenic mycelium there is the added advantage of improving the restricting of disease transmission by having another control technology in the same locale.

Where attractant mycopesticidal strains are utilized with insects, the infected insects carrying the fungal hyphae become a vector back into population, further dispersing the antimicrobial mycelium. The preconidial mycopesticidal mycelium can grow within or upon an insect, can be carried to another insect when they touch, or can grow upon organic debris allowing subsequent insect infestation from simple contact. Moreover, some insects will become immunocompromised from contact with *Metarhizium* based products, and the resultant lowered immunity allows for other pathogenic fungi to infect the now weakened insect. This secondary infectious suite of organisms can be more virulent than the *Metarhizium* itself. All these modes of action result in lowering the bio-burden and the pathogenic payloads that these zoonotic disease-bearing insects harbor. Multiple avenues of growth and infection are provided and could be further enhanced if the addition of conidia from entomopathogenic fungi were deployed, as part of the composition of insect control.

The preconidial mycelium of mycopesticidal fungi is grown in pure culture using standard techniques for in vitro propagation. Once inoculated onto a substrate such as grain or wood, the mycelia matures to a state prior to conidia formation. The window of utility extends from post-spore germination through all stages of mycelial growth prior to sporulation. The preconidial mycelium may be utilized as is or may be arrested in its development through means such as flash chilling, freeze-drying, air-drying, refractance window dehydration, cryogenics, refrigeration, gaseous cooling, gas affixation (nitrogen, carbon dioxide, ethylene) and packaged in spoilage-proof or sealed packages. Even with post-conidial cultures of entomopathogenic fungi, methods can be employed which will 'turn off' conidial formation and 'turn on' non-conidial mycelial growth, resulting in attractancy, phagostimulation, and in some cases trail following or swarming behavior.

The end-user facilitates opening the package and placing the exposed mycelia contents in the vicinity of recent pest activity. For use as an attractant, extracts of the preconidial mycelium may also be utilized. It is envisioned that the fungal attractants and/or pesticides may be used in conjunction with any type of appropriate trap or attractant disseminator or delivery system as is known to the art.

By combining an extract of mycelium from a fungus having antimicrobial and/or antiviral properties with an extract from the preconidial mycelium of an entomopathogenic fungus, the unique mixture can serve as a unique combination for mitigating disease transmittance. A novel agent or treatment that kills the contagion but also severely harms the human host, for instance, is neither medically practicable nor commercially attractive. However, a novel agent that neutralizes the bacterium, protozoa or virus being carried by an insect is both medically and commercially significant. Moreover, if the preconidial entomopathogenic fungi attracts and simultaneously carries an infectious agent that controls the insect while also reducing internal pathogens harmful to animals and crops, disease transmission vectors can be limited, arrested, or re-directed using these unique combinations.

The present invention thus provides improved products and methods wherein the fungal mycelium acts as food and attractant and/or as an ingested or contact insecticide, palatable enough that insects will readily consume it even in the presence of competing food sources, or otherwise repellent materials, with high recruitment of other insects among insects that exhibit such behavior. This results in multiple visits to a highly attractive (and potentially virulent) food, thereby providing numerous individual insect and/or colony vectors of inoculation.

The present invention further provides these and other advantages with improved control of insect pests using fungal compositions (mycopesticides and mycoattractants) having strong attractant properties and placing these attractant preconidial fungi in or around an object or area to be protected. The present invention also provides insecticidal foods and baits that utilize, as a toxicant, relatively innocuous and naturally occurring materials as the active agent, so as to control insects carrying zoonotic diseases without undue effect on the ecology. Alternatively, the present invention provides attractants that can be utilized with bio-control agents, environmentally benign biopesticides, chemical control agents including insect toxicants and pesticides, human modified organisms, viruses and bacteriophages, physical control agents such as mechanical and electrical devices and combinations thereof. It is to be expected that the number of sub-inventions and applications obvious to those skilled in the relevant arts is limited only by imagination and time, and any such derivative inventions and applications should be considered to be part of the invention disclosed herein. New zoonotic diseases and new disease controlling technologies will emerge and the inventions described herein are likely to enhance many future technologies.

Still further objects and advantages of the present invention will become more apparent from the following detailed description and appended claims.

Before explaining the disclosed embodiments of the present invention in detail, it is to be understood that the invention is not limited in its application to the details of the particular products and methods illustrated, since the invention is capable of other embodiments, including those embodiments that have not yet been reduced to practice and tested. In addition, the terminology used herein is for the purpose of description and not of limitation.

DESCRIPTION OF THE PREFERRED EMBODIMENTS

The concepts of "pathogens" and "pathogenic" (and the related "entomopathogens" and "entomopathogenic") have implications that extend well beyond the standard dictionary definition of "capable of causing disease or mortality." Some entomopathogenic fungi are widespread and cause no known affects whatsoever in their insect hosts; *Myrmicinosporidium durum* is illustrative of entomopathogenic fungi that cause few symptoms and are consequently hard to detect in the first place. Schmid-Hempel, P., *Parasites in Social Insects*, Princeton University Press, p. 83 (1998). Entomopathogenic fungi as used herein are those capable of infecting and parasitizing insects, regardless of their actual effect on the host. "Virulence" and "virulent strains" similarly have meanings extending beyond the dictionary definition of extremely infectious, malignant or poisonous. Parasite virulence and host resistance determine how host and parasite interact in ecological time and how they co-evolve. Virulence is often defined as an increase in the host mortality rate as a result of the parasite's presence. But reduced host fecundity, parasite replication rate within the host, and several other measures have also been used. Virulence should in principle also include instances where the behavior of the host is manipulated by the parasite to increase the probability of its successful transmission and where it places the individual host at greater risk. See Schmid-Hempel, supra, pp. 237-238. Here the terms virulent and virulence are used in a broad sense that encompasses all of these meanings. It will refer to processes which are caused by entomopathogenic fungi and which lead to a reduction in some component of the host's fitness or an increase in mortality. Virulence and resistance are therefore properties that emerge as a result of host-parasite interaction in a given environment. Expression of virulence is as diverse as the lifestyles and characteristics of the insect hosts and the entomopathogenic fungi themselves.

The present invention provides improved mycoattractants and mycopesticides (fungal mycelia utilized as insect attractants or baits and/or insect biopesticides, after mycology, the study of fungi) to control zoonotic diseases harbored by and vectored by insects and non-insect arthropods.

Laboratory procedures for testing entomopathogenic fungi often involve procedures inapplicable in the field, such as "dusting" of many or all of the insects with spores or forced contact with conidia in petri dishes (itself a form a stress). Insects infected with mycopesticidal spores are often rejected or isolated from the general population, thus limiting the further spreading of the fungal disease. Wilson, E. O., *The Insect Societies*, The Belknap Press of Harvard University Press, pp. 103-119 (1974). For these and other reasons, conidia of entomopathogenic fungi have often been much more effective under laboratory conditions than in the field.

It was found that the "fragrance signature" of the mycopesticidal mycelium is a strong attractant to insects prior to conidia formation. The genesis for these findings was the initial observation that the odor of the cultured mycelium was similarly pleasing to humans when preconidial and repellant after conidia formation; smell and the fragrance signatures of mycelium are utilized by the present inventor as indicators of the health of the mycelium in large scale production of gourmet and medicinal mushrooms, whereas "petri dish mycologists" and entomologists studying pathogenic fungi are typically trained not to sniff or inhale from the cultures. In fact, most mycologists are trained not to do so, as standard laboratory protocol, because such actions could be a threat to their health. It was noted such fragrance signatures are lost when mycelium is grown via liquid fermentation—this may be due to such fragrance signatures being "washed away" or due to the greatly reduced nutritional base available to the mycelium in liquid fermentation as compared to solid substrates such as grain or wood. "Outgassing" of $CO_2$ and attractant molecules by the mycelium is believed by the present inventor to be responsible for at least some portion of the attractant value. It was also noted that liquid fermentation utilizing a typical fermenter with bubbled air mixing will promote conidia formation, with such conidia production being even further promoted by the common commercial practice of utilizing bubbled or chemically generated oxygen.

In addition to the attractant properties and phagostimulatory (feeding stimulating) properties of preconidial mycopesticides, it was further found that pathogenic fungal control agents are much more effective when preconidial (pre-sporulation) mycopesticidal mycelium is ingested and/or contacted by the targeted insect as compared to conidia or post-sporulation mycelium/conidia offered to targeted insects for the purpose of infection by contact. The preconidial mycopesticidal mycelium is thought to be an effective attractant and/or pathogen, at least in part, because it is a preferred food, particularly for social insects and other fungi-feeding insects.

The preconidial mycelium has been observed to be a preferred food source that stimulates "grazing" of the fungi on wood and/or grain, scattering of the fungus, and caching of the fungus by social insects including termites, carpenter ants, and fire ants. Novel behaviors observed in the social insects include that of Formosan termites (*Coptotermes formosanus*) ignoring available wood while preferring to set up "housekeeping" in the mycelium, and fire ants and carpenter ants moving the preconidial fungi around the feeding arena and/or into nest chambers. Social insect colonies have been described as "factory fortresses." See Wilson, supra, (1974); Oster, G. F. and E. O. Wilson, *Caste and Ecology in the Social Insects*, Princeton University Press (1978); Schmid-Hempel, supra, (1998). While it may be difficult for a parasite to "break into the fortress" and gain access to a colony, once inside, the opportunities abound (Schmid-Hempel, supra, p. 77 (1998). Similarly, once the social insect defenses have been penetrated via the attractiveness of preconidial mycopesticidal mycelium, the opportunities abound for further inoculation and spread of the preconidial mycelium both orally and dermally, as well as optional introduction of other bio-control agents or chemical toxicants. Novel and unique features of the invention include the use of a mycopesticidal mycelium or extract as an attractant, the use of a mycopesticidal vector of parasitization that relies directly on hyphal fragments to infect both insects and/or social insect housing structures, the use of high levels of carbon dioxide to grow and maintain preconidial mycelium, the use of late sporulating strains to prolong the attractive preconidial state, the use of various methods to arrest development at the preconidial stage and/or to facilitate growth, packaging, shipping, and convenient application by an end user, and various improvements in methods of attracting, controlling, preventing, eradicating, and limiting the spread of disease vectoring insects and arthropods.

Preconidial mycelium has proven to be highly effective by ingestion or contact, with the exudate-excreting mycelial hyphae already being in a state of active growth when ingested or contacted. The preconidial mycelium is thought by the present inventor to function both as a "fungal food of infection" and as a contact insecticide. Efficacy as a contact insecticide is believed to be aided by the somewhat "sticky" nature of mycelium. While not wishing to be bound by any theories or hypotheses, the present inventor believes various possible vectors for further spread and growth of the preconidial mycelium include: incidental contact and adhesion; feeding and "sloppy eating" which may spread hyphae to insect cuticles; food caching; individual and social grooming; aerial transmission of hyphal fragments (as dry hyphal fragments are much less dense than spores, they easily become airborne and spread); inhalation; incidental contact; trophallaxis (exchange of liquid food); proctodeal trophallaxis (exchange of anal excrement by termites and others); cannibalism; mating; contact with cadavers; inoculation of housing structures; etc. Mycopesticidal species are thought by the present inventor to employ various pathogenic modes when transmitted via ingestion or contact with mycelial hyphae, including: infection via the cuticle, the tracheal openings, the alimentary canal, or wounds with resultant growth upon the insect and resultant depletion of host resources and/or damage or destruction of host tissue; production of antibiotics, antibacterials, and antiprotozoans with the resultant death of microflora within the gut; production of anti-fungal compounds affecting symbiotic and associated fungi; production of toxic substances by the entomopathogens; suppression or disruption of the immune system response; etc.

Since mites are non-insect arthropods and mites have long been observed as a pest to mushroom crops, both at the mycelial stage and when mushrooms subsequently form (Stamets, P. and Chilton, J., *The Mushroom Cultivator*, Agarikon Press, 1983), and since mites can be parasitized by entomopathogenic fungi, the use of preconidial mycelium of entomopathogenic fungi to attract and control mites, and the bacterial "blotch" they inflict to mushroom crops is an important new strategy for limiting losses in mushroom farms, or wherever mites inflict damage and cause bacterial diseases. The same methods described herein can be readily adapted for limiting mites and the diseases they spread to plants, thus protecting crops.

In utilizing wood and other cellulose containing materials, one preferred method is to grow the pre-sporulation mycopesticidal mycelium on wooden or other cellulosic materials "bait blocks" or "bait traps." Bait chips, blocks, or traps (or optionally other forms such as pellets, extruded pellets, mats, fabrics, ropes, etc.), optionally soaked with a malt solution, honey, or other sugar and/or nutrient solution, are infused and/or inoculated with preconidial mycopesticidal mycelia which then spread the infection to the targeted insect pests via any of the mycelium vectors described herein. Biodegradable bait traps may be made of, or have components made of various cellulosic, ligninic, celluloligninic, carbohydrate, and fiber materials including but not limited to: paper products and cardboard; wood and sawdust; corn cobs and cornstalks; chip board; fibers such as jute, flax, sisal, reeds, grasses, bamboo, papyrus, and coconut fibers; nut casings such as peanuts, almonds, walnuts, sunflower, pecans, etc.; seed hulls such as cottonseed hulls; agricultural products and byproducts such as hemp, cereal straws, sugar cane bagasse, soybean roughage, coffee wastes, tea wastes, cactus wastes, banana fronds, and palm leaves; industrial byproducts such as fiberized rag stock; combinations thereof, and numerous other forest agricultural, and industrial products and byproducts which will host mycelium and are degradable by mycopesticidal fungi. Where rapid biodegradability of the traps is desired, materials such as cardboard or paper may be utilized. For insects including carpenter ants or termites, cockroaches, etc., the bait blocks preferably contain channels, tunnels, grooves, ridges, holes, or perforations specifically sized to allow entry by the targeted species and or its brood, pupae and/or larvae. Inoculation may, for example, be accomplished via grain in the channels and the blocks may optionally be layered or "wafered" together. A composite, layered or intertwined matrix of materials may be utilized, with one set of materials infused with the attractant extract of an entomopathogenic species and the other containing active or metabolically arrested preconidial mycelium. A multiplicity of such bait blocks or traps or barriers may be utilized to protect structures, agricultural locations, hospitals, dormitories, etc. A fungal matrix with a plurality of pre-sporulating mycopesticidal fungal species and/or extracts that are highly attractant to the targeted pest insect, combined with antimicrobial, antiprotozoan, and anti-viral ingredients, may be created so that the targeted pest is drawn close to a locus where the insect pest becomes infected and is harmed or killed by the selected fungi or via other means.

The wooden, cardboard, or lignin-cellulose baits and bait traps may optionally be frozen, dried or freeze-dried, or gaseously treated to arrest growth until activated by moisture and air exposure. Either the myceliated bait may be presented to the insect, with rehydration and recovery taking place, for example, within the central nests of social insects, or placed in the migration corridors of traveling insects. The bait block may be rehydrated prior to or during use or presented fresh.

The highly attractive nature of preconidial mycopesticidal mycelium indicates that essences extracted from preconidial mycelium of mycopesticidal fungi can be expected to be highly attractive in and of themselves, and in conjunction, associated compounds may possess innate antimicrobial or antiviral properties, and thereby similarly useful alone or in conjunction with biological, chemical, mechanical and/or electronic insect control agents, useful as masking agents for otherwise repellant toxicants for insect pests, and useful as "distractants" in diverting insects away from sites that need protection. Such essences include extracts, concentrates, fragrances, derivatives, active constituents, etc. and may be prepared by methods known to the art including extraction with water, alcohols, organic solvents and supercritical fluids such as $CO_2$, etc. Extracts may also be prepared via steam distillation of volatile components, similar to the preparation of "essential oils" from flowers and herbs. Suitable alcohols include those containing from 1 to 10 carbon atoms, such as, for example, methanol, ethanol, isopropanol, n-propanol, n-butanol, 2-butanol, 2-methyl-1-propanol (t-butanol), ethylene glycol, glycerol, etc. Suitable organic solvents include: unsubstituted organic solvents containing from 1 to 16 carbon atoms such as alkanes containing from 1 to 16 carbon atoms; alkenes containing from 2 to 16 carbon atoms; alkynes containing from 2 to 16 carbon atoms; and aromatic compounds containing from 5 to 14 carbon atoms, for example, benzene, cyclohexane, cyclopentane, methylcyclohexane, pentanes, hexanes, heptanes, 2,2,4-trimethylpentane, toluene, xylenes, etc.; ketones containing from 3 to 13 carbon atoms such as, for example, acetone, 2-butanone, 3-pentanone, 4-methyl-2-pentanone, etc.; ethers containing from 2 to 15 carbon atoms such as such as t-butyl methyl ether, 1,4-dioxane, diethyl ether, tetrahydrofuran, etc.; esters containing from 2 to 18 carbon atoms such as, for example, methyl formate, ethyl acetate and butyl acetate; nitriles containing from 2 to 12 carbon atoms such as, for example acetonitrile, proprionitrile, benzonitrile, etc.; amides containing from 1 to 15 carbon atoms such as, for example, formamide, N,N-dimethylformamide, N,N-dimethylacetamide; amines and nitrogen-containing heterocycles containing from 1 to 10 carbon atoms such as pyrrolidine, 1-methyl-2-pyrrolidinone, pyridine, etc.; halogen substituted organic solvents containing from 1 to 14 carbon atoms such as, for example, bromotrichloromethane, carbon tetrachloride, chlorobenzene, chloroform, 1,2-dichloroethane, dichloromethane, 1-chlorobutane, trichloroethylene, tetrachloroethylene, 1,2-dichlorobenzene, 1,2,4-trichlorobenzene, 1,1,2-trichlorotrifluoroethane, etc.; alkoxy, aryloxy, cyloalkyl, aryl, alkaryl and aralkyl substituted organic solvents containing from 3 to 13 carbon atoms such as, for example, 2-butoxyethanol, 2-ethoxyethanol, ethylene glycol dimethyl ether, 2-methoxyethanol, 2-methoxyethyl ether, 2-ethoxyethyl ether, etc.; acids containing from 1 to 10 carbon atoms such as acetic acid, trifluroacetic acid, etc.; carbon disulfide, methyl sulfoxide, nitromethane and combinations thereof. Extracts may also be prepared via sequential extraction with any combination of the above solvents. The extracts may optionally be combined with fixatives, enhancing agents, oils, alcohols, solvents, glycerin, water and other substances that aid in distributing the attractant and/or enhancing its fragrance value. Essences extracted from preconidial mycelium of mycopesticidal fungi can be used as a protectant or distractants, luring insects away from a locus and preventing insect damage to a locus, habitat, structure, crop, animal, human, etc. Such attractant essences and extracts may be utilized with wicking agents, sprayers, etc. to enhance their effectiveness. Preliminary indications are that such attractant molecules are polar and thus best extracted with polar and/or hydrophilic solvents. The present invention in conjunction with the principles of chemical ecology and evolutionary biology raise the possibility that the entomopathogenic fungal species produce attractant molecules (or more likely, groups of attractant molecules) that have co-evolved over evolutionary time with species of insects or groups of insects. Such attractant molecules, optimized for one species of insect, may well show attractant properties to larger groups of insects. Since all these fungi produce fatty acids, particularly linoleic acids, these and other sterols, all have within them some of these attractant molecules. It will be apparent to those skilled in the art that numerous such molecules or groups of attractant molecules may be isolated and/or characterized from the preconidial fungi of the present invention and as such should be considered part of the present invention.

The preconidial mycelium or extracts thereof may be utilized solely as an attractant for various purposes. For example, preconidial mycelium may be utilized to affect insect choice of geographical location, destructive and zoonotic disease bearing pests being attracted and distracted away from structures, agricultural plots, hospitals, army barracks, theaters, convention centers, schools, etc. Fungal species and strains particularly attractive to beneficial insects may be utilized to attract desired insect species, the fungi acting as a biological catalyst to steer the course of the insect community evolution. Alternatively, varying insects may simply be attracted to occupy the environment and thus forestall pest invasions. It is known that virulence of entomopathogenic strains varies widely in the laboratory when tested via typical conidia based assays, with mortalities from 0% to 100% being recorded dependent upon such factors as number of conidia applied per insect and the insect species and the entomopathogenic species and strain being tested. Similar results may be expected for preconidial formulations, although a greater effectiveness in general may be expected since lack of virulence in the typical bioassay is often related to a failure of conidia to adhere to the insect and/or failure of the conidia to germinate as discussed above. Thus strains of "pathogenic" or "entomopathogenic" fungal species may be selected which actually vary in virulence from non-pathogenic to relatively weakly virulent to strongly virulent. Non-virulent preconidial mycelium may be used to attract beneficial predator and parasitic insects. Alternatively, non-virulent strains may be utilized as a distractants, for example attracting Coccinellidae, the lady beetles, away from areas where they may be a pest (such as office buildings) and into "ladybug motels." Alternatively, virulent strains may be utilized as an olfactory attractant but made inaccessible with devices such as screens or slots.

The mycoattractants and/or mycopesticides disclosed herein may also be optionally enhanced by the use of other baits, foods, attractants, arrestants, feeding stimulants, sex pheromones, aggregating pheromones, trail pheromones, etc. For example, a bait box overgrown with preconidial mycopesticidal mycelium might contain other attractants and contact pesticides, and contain antimicrobial, antiprotozoa, and antiviral ingredients.

Attractant preconidial or pre-sporulation mycelium (virulent, weakly virulent and/or non-virulent) or extracts may also be utilized in conjunction with other biological organisms, chemical pesticides and physical control agents as part of integrated pest management (IPM) systems that incorporate multiple pest control tools and seek to minimize pesticide inputs. The use of attractant fungi in combination with other insect control agents affords the advantage of attracting the targeted pest to a locus, which, by other treatments, results in sterility and/or death of the targeted insect.

The weakened immune systems of pest insects exposed to pathogenic or virulent mycopesticidal organisms allows other beneficial parasitic and predator species to flourish. Such beneficial biological control agents include microbial pathogens, predator insects (entomophagous insects which eat other insects) and parasitic insects (those which reproduce by laying eggs in or on any stage the host insect, from egg to adult), as well as non-insect predators such as birds and beneficial nematodes, spiders, and mites. Examples of biological control agents include: entomopathogenic fungal species and their spores; *Bacillus thuringiensis, B. popilliae, B. subtilis,* and *Pseudomonas*; fire ant parasites (such as Phorid flies); fly parasites including wasps such as *Muscidifurax raptorellus* and *Spalangia cameroni*; hister beetles such as *Carcinops pumilio*; dung beetles including *Onthophagus* spp.; parasitic nematodes such as *Steinernema feltiae*; cockroach parasites such as *Anastatus tenuipes, Aprostocetus hagenowii, Comperia merceti* and nematodes; lacewings; ladybugs; bigeyed bugs; damsel bugs; praying mantises; *Trichogramma* wasps; beneficial mites; ant parasites; flea parasites; lygus bug parasites; mealybug; aphid and whitefly parasites and predators; caterpillar parasites; spider mite predators; looper parasites; diamondback and moth parasites; scale parasites and predators; mite parasites and predators; etc. Strains may be selected, utilizing those methods known to the art, for virulence against the targeted pest insects and/or non-virulence or weak virulence against predator insect species as well as such qualities as resistance to pesticides, etc. If desired, resistant predator or parasitic species may be selected for, bred and released to further control the targeted pest species. Blends of beneficial insect attractant plants and habitat plants may also be utilized in combination with antimicrobial, antiprotozoa and antiviral agents. This multiplatform approach is not limited to just one pairing of fungus, one beneficial organism and one anti-disease component, but as many permutations as can be implemented for the purpose of creating an environmental equilibrium affording long-term protection of the inhabitants from other insects, animals, and plants. Other fungal attractants may also be optionally utilized. Thus, a combination of the preconidial mycelium of mycopesticidal species and Oyster mushrooms (*Pleurotus* and *Hypsizygus* species, the mycelium and mushrooms of which are very attractive to Phorid flies) might be utilized to attract phorid flies in the genus *Pseudacteon* that parasitize fire ants and leaf-cutter ants.

The preconidial mycopesticides (both virulent and non-virulent strains) and extracts may also be utilized as "masking agents" as well as attractants in conjunction with insect chemical control agents, toxicants and/or pesticides, thereby preventing aversion to other effective compounds that may otherwise repel the insect. Chemical control agents include insect toxicants, poisons, regulators and pesticides as well as the chemicals (semiochemicals) which mediate interactions between individuals of a insect species (pheromones) or between co-evolved species (allelochemicals, such as kairomones and allomones). Residual (persistent), non-residual (nonpersistent), and solid, liquid, aerosol or fog contact chemical control agents include, by way of example but not of limitation: stomach poisons such as sulfluramid; pyrethrum extracts; natural and synthetic pyrethroids; parapyrethroids (non-ester pyrethroids) such as silafluofen, etofenprox and cyfluthrin; pyrethroid analogs such as fenvalerate, permethrin, phenproparthrin, fluvalinate, flucythrinate, fenproparthrin, cypermethrin, deltamethrin, tralomethrin, cyclopro- thrin, esfenvalerate and zeta-cypermethrin; allethrins; lethanes; nicotinyl compounds such as imidacloprid; phenylpyrazoles such as fipronil; amidinohydrazones such as hydramethylnon (a respiratory poison); abamectin (a mixture of avermectins, insecticidal or anthelmintic compounds derived from the soil bacterium *Streptomyces avermitilis*); Spinosad (spinosyn metabolites produced by *S. spinosa*); artemisinin from *Artemesia* plants; nitromethylenes; carbamates such as propoxur and fenoxycarb; organophosphates such as acephate and chlorpyrifos; pyriproxyfen; insect growth regulators; synthesis inhibitors; chitin synthesis inhibitors such as hexaflumuron and diflubenzuron; mineral acids such as boric acid; alcohols and organic solvents; elements such as sulfur; and combinations thereof. Such chemical control agents may optionally be combined with synergistic compounds that increase the toxicity and/or enhance the biological activity of another, for example by inhibiting the enzymatic detoxification of insecticides by microsomal oxidases or hydrolytic enzymes such as esterases. Examples of synergists include: methylenedioxyphenyl (MDP) compounds such as piperonyl butoxide, piperonal bis-(2,2-(butoxyethoxy)-ethyl)acetal, 1,2-methylenedioxynaphthalene, tropital (polyalkoxy acetal of piperonaldehyde) and sesamex; trisubstituted aliphatic and aromatic phosphates such as TOCP (tri-o-cresyl phosphate); a number of non-insecticidal carbamates; EPN (O-ethyl-O-p-nitrophenyl phenylphosphonothionate); sulfoxide; propynyl ethers; p-nitrobenzyl thiocyanate; 2-((4,6-dichloro-2-biphenylyl)-oxy) triethylamine; 2-(diethylamino)ethyl 2,2-diphenyl pentanoate; 2-propynyl 4-chloro-2-nitrophenyl ether; N-octyl bicycloheptane dicarboximide; and n-propyl isome. Use of attractant or attractant/pesticidal preconidial mycelium or extracts, in combination with antibiotics and antivirals, enables the use of extremely small amounts of toxicant or pesticide to effectively control insect populations and the diseases they transmit. Alternatively, sublethal doses of pesticides or toxicants may be included to enhance the activity and virulence of the mycopesticidal species; or pathogenic and virulent preconidial mycelium may be utilized as a preconditioning treatment, increasing the susceptibility to and/or potentiating the virulence of other agents (such as pesticidal chemicals, other mycopesticides, or bacteriological, plasmodial and viral compounds). Lethal or sublethal doses of insect toxicant and antibiotic materials may optionally be encapsulated within an attractant extract or mycelia-impregnated (virulent or non-virulent) sheath, coating, covering, encapsulative material, protective and/or time degrading envelope, or the toxin may surround, cover or encapsulate a mycelial substance or extract of strong attractive and/or mycopesticidal properties, or such may be simply mixed.

The mycoattractants and mycopesticides of the present invention may also be combined with physical control agents. Physical control agents are devices that destroy insects directly or act indirectly as barriers, excluders, or collectors. Physical controls include the use of mechanical and electrical devices, heat, light, electricity, X-rays, lasers, and so on, to kill insects directly, reduce their reproductive capacity, or to attract them to something that will kill them. Various physical means may be employed to act as barriers to insect movement. Sticky materials in which insects become hopelessly entangled may be used in the form of flypaper or coated objects and materials. Traps may be used for control, survey, and surveillance purposes. Control traps may be used in conjunction with mycoattractants and with some means of killing the insects that enter (e.g., a pesticide or an electrically charged grid). Mosquito or bed nets can be impregnated to attract disease carrying insects or arthropods whereupon contact, they are trapped. If not trapped, the escaping insects and arthropods, post contact, may have their pathogenic payloads reduced. This approach has many merits—as the insects and arthropods live after making contact, but now represent less of a threat for infection and disease transmission.

The preconidial mycelium on manufactured, compressed pellets or granules, with or without additional liquid(s), can be used for applications in agricultural, forest, industrial and/or domestic settings, wherein the myceliated pellets become loci for attracting the target pests, and thus through contact become infected. Trends in mushroom spawn for gourmet and bioremediation purposes have long been evolving toward pelletized or granular spawn while mycopesticidal spore technology similarly has evolved toward granulated or spray formulations. Various forms of pelletized spawn, coated compositions, granules and dusts are known, including those formed from nutrients, with or without carriers and binders, such as peat moss, vermiculite, alginate gel, wheat bran, calcium salts, hydrophilic materials such as hydrogel, perlite, diatomaceous earth, mineral wool, clay, polymers, biopolymers and starch, including wettable powders, emulsifiable concentrates, starch and/or biopolymer coatings, etc. Pelletized spawn is specifically designed to accelerate the colonization process subsequent to inoculation. Idealized pelletized spawn seeks a balance between surface area, nutritional content, and gas exchange and enables easy dispersal of mycelium throughout the substrate, quick recovery from the concussion of inoculation, and sustained growth of mycelium sufficient to fully colonize the substrate. See Stamets and Chilton, supra, pp. 141-142 and U.S. Pat. No. 4,551,165 (1985) to Warner, U.S. Pat. No. 4,668,512 (1987) to Lewis et al., U.S. Pat. No. 4,724,147 (1988) to Marois, et al., U.S. Pat. No. 4,818,530 (1989) to Marois, et al., U.S. Pat. No. 5,068,105 (1991) to Lewis, et al., U.S. Pat. No. 5,786,188 (1998) to Lamar, et al., and U.S. Pat. No. 6,143,549 (2000) to Lamar, et al. Liquid sprays include the above wettable powders and emulsifiable concentrates, water-dispersible granules, aqueous solutions, emulsions such as oil-in-water and water-in-oil emulsions, dispersions, suspoemulsions, microemulsions, microcapsules, etc. Wettable powders are formulations that are typically uniformly dispersible in water and also contain surface-active agents (surfactants) such as wetting agents, emulsifiers and dispersing agents. Emulsifiable concentrates are prepared with organic solvents and/or one or more emulsifiers. Sticking agents such as oils, gelatin, gums, tackifiers and adhesives may be used to improve the adhesion of the spray. Humectants may also be used to decrease the rate of evaporation, including for example glycols having from 3 to 10 carbon atoms and glycerin and solutes such as salts or sugars in water.

For large scale application, fabric or fiber cloths, landscaping cloths, geofabrics, soil blankets and rugs, mats, mattings, bags, gabions, fiber logs, fiber bricks, fiber ropes, nettings, felts, tatamis, bags, baskets, etc. made of biodegradable materials infused with preconidial mycelia of mycopesticidal species, combined with antimicrobial and antiviral agents, may be utilized as a mechanism for attracting, preventing, killing or limiting the spread of targeted insects (or of attracting beneficial insects) and zoonotic diseases. Thus, for example, barriers or "aprons" of mycopesticidal mycelium grown on straw, coconut fiber, wood, paper, cardboard or the other forestry and agricultural products, wastes and cellulose sources noted above might be placed around Oak trees to protect from beetles and introduced wilts such as *Phytophthora* and *Ceratocystis fagacearum* or around pine trees or stands to protect from destructive fungi and diseases carried by bark beetles. Similarly, such mycopesticidal aprons might be utilized to protect other trees, shrubs, grasslands, rivers and streams, estuaries, riparian zones, agricultural fields, gardens and crops, structures, communities, habitats and sensitive ecosystems. Such preconidial mycopesticidal aprons might alternatively be used to attract pest insects to a site whereupon other biological, chemical, mechanical, electrical and/or other insect reducing treatments become more effective. Conversely, creation of buffers utilizing non-virulent strains selected for attractiveness to beneficial insects can be used to attract beneficial species, which naturally parasitize problem insects.

Alternatively, woodchips, grains, hydromulch and other substrates infused with preconidial mycelium may be utilized in spray hydroseeders or mobile hydroseeders. Agricultural equipment may be utilized to inoculate fields and agricultural wastes. The mycopesticidal fungi may also optionally be utilized in conjunction with saprophytic fungi and mycorrhizal fungi to enhance soils and agricultural yields ("companion cultivation" of beneficial fungi). Mycopesticidal species are also useful in the mycoremediation (fungal bioremediation) of various sites. As one example, reclaimed logging roads could become perimeter-barriers which could forestall and/or prevent beetle-plagues from devastating forestlands by infusing mycomats or hydromulches with species-specific pathogenic fungi (and optionally saprophytic and mycorrhizal fungi), combined with antimicrobial or antiviral agents, while simultaneously retaining other benefits of mycofiltration. Thus, mycopesticidal species such as *Metarhizium, Beauveria* and *Cordyceps*, mycorrhizal mycopesticidal fungi such as *Laccaria*, and myconematicidal saprophytic fungi such as *Pleurotus* might be combined with ectomycorrhizal and endomycorrhizal species and saprophytic fungi to provide simultaneous insect control, road reclamation and protection of streams from silt runoff and disease control. As *Hypholoma capnoides*, a premier wood chip decomposer, mycelium has been observed to be repellant to insects, stretches of insect repellant barriers may be combined with attractant mycopesticidal kill and/or control zones for insects such as wood-boring beetles. Similarly, control of agricultural runoff utilizing saprophytic fungi on agricultural wastes might be combined with the present mycoattractant and/or mycopesticidal applications, while in combination with antimicrobial and antiviral agents, to limit the spread of disease.

In general, preferred mycopesticidal species as pathogens are somewhat slow-acting (that is, not immediately fatal) so as to avoid bait shyness and to avoid learning effects in social insects before individuals have distributed mycelium to all other members of the colony. To effect control of the Formosan subterranean termite (*Coptotermes formosanus*) colonies, bait chemicals must kill slowly enough to allow foraging termites to return to the colony and spread the toxin to other colony members. Wright et al., "Growth response of *Metarhizium anisopliae* to two Formosan subterranean termite nest volatiles, naphthalene and fenchone," *Mycologia,* 92(1): pp. 42-45 (2000) and the references therein. Bait shyness and other colony defense mechanisms such as segregation or avoidance of infected nestmates or necrophoretic behavior by the workers (i.e., removal of dead nestmates) serve as a means of defense against the spread of such pathogens when the targeted insect dies too quickly. For example, in general, queen fire ants will not feed on new foodstuffs until the food is first sampled by foragers or workers or members of expendable classes and deemed safe after a two or three day waiting period. Note, however, this general pattern may not always apply to the highly attractive mycoattractants and mycopesticides disclosed herein. Preconidial mycelium strains may be selected for virulence after an appropriate time period. In many applications it may be preferable to utilize a mixture or matrix of several species or strains of entomopathogenic fungus with different characteristics, maturation and growth rates including strains with delayed sporulation (and thereby prolonged attractant value) while in other applications a single species may be preferred. Similarly, with reference to a single species, a mixture of strains or a single strain may be utilized. A mixture of species and/or strains both allows the targeted insects to choose the species to which they are most attracted and provides for the possibility of simultaneous infection and insect plagues from multiple virulent species and strains. This makes tolerance or resistance of the insect or arthropod much more unlikely compared to just using one strain or antimicrobial agent.

Those skilled in the art will recognize that numerous entomogenous and entomopathogenic fungal species are known to the art and the above preconidial mycoattractant and mycopesticidal methods and products may be favorably applied to many or all such species, and it is the intent of the inventor that the invention be understood to cover such. Suitable entomopathogenic fungi include: the Deuteromycetes *Metarhizium, Beauveria, Paecilomyces, Hirsutella, Verticillium, Culicinomyces, Nomuraea, Aspergillus* and other fungi imperfecti; sexually reproducing fungi such as the Ascomycetes *Cordyceps, Ophiocordyceps, Ascosphaera, Torrubiella, Hypocrella* and its *Aschersonia* anamorph, and the Pyrenomycete *Laboulbenia hageni*; the Basidiomycetes such as *Laccaria, Pleurotus, Fomes, Fomitopsis, Hypsizygus, Piptoporus, Lenzites, Ganoderma*, and combinations thereof. The Entomophthoracae including *Entomophaga, Massospora, Neozygites, Zoophthora, Pandora* and other Phycomycetes are also considered to be within the scope of the invention. Also included are such entomopathogenic species that have been genetically modified to be more virulent (including those modified via mutagenesis, hybridization and recombinant DNA techniques).

By way of example, but not of limitation, mycopesticidal species include *Metarhizium anisopliae* ("green muscarine"), *Metarhizium flaviride, Beauveria bassiana* ("white muscarine"), *Beauveria brongniartii, Paecilomyces farinosus, Paecilomyces fumosoroseus, Verticillium lecanii, Hirsutella citriformis, Hirsutella thompsoni, Aschersonia aleyrodis, Entomophaga grylli, Entomophaga maimaiga, Entomophaga muscae, Entomophaga praxibulli, Entomophthora plutellae, Zoophthora radicans, Neozygites floridana, Nomuraea rileyi, Pandora neoaphidis, Tolypocladium cylindrosporum, Culicinomyces clavosporus* and *Lagenidium giganteum*, the wide variety of *Cordyceps* (and *Ophiocordyceps*) and its ascomycetous forms including *Cordyceps variabilis, Cordyceps facis, Cordyceps (Elaphocordyceps) subsessilis, Cordyceps myrmecophila, Cordyceps sphecocephala, Cordyceps entomorrhiza, Cordyceps gracilis, Cordyceps militaris, Cordyceps washingtonensis, Cordyceps melolanthae, Cordyceps ravenelii, Cordyceps unilateralis, Cordyceps sinensis* and *Cordyceps clavulata*, and mycorrhizal species such as *Laccaria bicolor*. Other mycopesticidal species will be apparent to those skilled in the art.

The concepts of "preconidial" and "spores" or "conidia" are complex, containing a number of different forms and specialized structures for reproduction of the fungi. Many fungi are pleomorphic, that is, one fungus may produce several sorts of spores, which may or may not be coincident in time. With regard to the sexually reproducing *Cordyceps, Laccaria* and other "fungi perfecti," preconidial or pre-sporulation refers to the pre-fruiting state. The term "preconidial" or "pre-sporulation" has a somewhat different meaning with regard to the sexually reproducing fungi than with most other entomopathogenic fungi, as sexually reproducing fungi are "fungi perfecti" or mushroom fungi, whereas the non-mushroom fungi such as *Beauveria* and *Metarhizium* are the more primitive "fungi imperfecti." The situation is complicated by the fact that entomophthoralean fungi have complex life cycles involving non-sexual conidia and sexual resting spores. The situation is further complicated by the fact that some or all *Cordyceps* fungi are dimorphic and have a teleomorph (the sexual perfect form or morph, e.g. that characterized by sexual spores including ascospores and basidiospores) and one or more anamorphs (the asexual imperfect form or morph, e.g. characterized by the presence or absence of conidia) with conidial stages within the imperfect fungal genera including *Beauveria, Metarhizium, Paecilomyces, Hirsutella, Verticillium, Aspergillus, Akanthomyces, Desmidiospora, Hymenostilbe, Mariannaea, Nomuraea, Paraisaria, Tolypocladium, Spicaria (=Isaria)* and *Botrytis*. For example, *Cordyceps subsessilis* is the perfect form of *Tolypocladium inflatum*, an anamorph (imperfect) form which produces cyclosporin. Hodge et al., *Mycologia* 88(5): 715-719 (1996). *Cordyceps militaris* (Fr.) Lk. is also thought to be dimorphic, the conidial stage of which is believed to be a *Cephalosporium*. *Cordyceps unilateralis* seems specific on the Camponotinii, while *Hirsutella sporodochialis* is probably an anamorph of *Cordyceps unilateralis* specific on *Polyrhachis*. Schmid-Hempel, supra, p. 43. The situation is further complicated in that conidia, without asci, have often been observed in Cordyceps by the inventor. DNA studies are expected to better elucidate these relationships. As used herein, unless otherwise specified, preconidial or pre-sporulation mycelium of sexually reproducing fungi refers to the pre-sporulation mycelial stage of the mushrooms, including any preconidial imperfect stages and any preconidial sclerotia or microsclerotia.

It is further expected that the preconidial products and methods may, with no more than routine experimentation, prove useful against presocial, parasocial, subsocial and nonsocial insects including semisocial, quasisocial, communal and solitary insect pests such as: cockroaches including American, German, Surinam, brown-banded, smokybrown, and Asian cockroaches; grasshoppers and locusts; crickets including mole cricket, Mormon crickets (actually a long-horned grasshopper); beetles, beetle grubs and beetle larvae including Colorado potato beetle (*Leptinotarsa decemlineata*) and other potato beetles, Mexican bean beetle, Japanese beetle, cereal leaf beetle, darkling beetle (lesser mealworm); moths including Gypsy moths (*Lymantria dispar*) and Gypsy moth larvae, diamondback moths (*Plutella xylostella*), codling moth (*Laspeyresia pomonella*), Douglas fir tussock moth (*Orgyia pseudotsugata*), western spruce budworm (*Choristoneura occidentalis*), and grape berry moths (*Lobesia lobina*); flies and fly larvae; springtails; large centipedes; shield centipedes; millipedes; European corn borers (*Ostrinia nubilalis*); Asiatic corn borers; caterpillars including velvet-bean caterpillar (*Anticarsia gemmatalis*), and other caterpillars and larvae of the Lepidoptera; whiteflies (*Dialeurodes* and *Bemisia* spp.) including sweet potato whiteflies, and silverleaf whiteflies; thrips (*Thrips* spp.) including melon thrips (*Thrips palm*), and western flower thrips (*Frankliniella occidentalis*); aphids including Russian wheat aphid; spider mites (*Tetranychus* spp.); mealybugs including citrus mealybug (*Planococcus citri*) and solanum mealybug (*Pseudococcus solani*); boll weevils, black vine weevils (*Otiorhynchus sulcatus*), European pecan weevils (*Curculio caryae*); mosquitoes; wasps; cotton fleahoppers; pasture scarabs such as *Adoryphorus couloni* and other Scarabaeidae; spittle bug (*Mahanarva posticata*); corn earworm (*Helicoverpa zea*); American bollworm (*Heliothis armigera*); armyworms including *Pseudaletia unipuncta*, fall armyworm (*Spodoptera frugiperda*), southern armyworm (*Spodoptera eridania*), beet armyworm (*Spodoptera exigua*), and yellow-striped armyworm (*Spodoptera ornithogalli*); black cutworm (*Agrotis ipsilon*); tobacco hornworm (*Manduco Sexta*); tobacco budworm (*Helicoverpa* (syn. *Helicoverpa*) *virescens*); sugar cane froghopper; rice brown planthopper; earwigs; loopers including cabbage looper (*Trichoplusia ni*) soybean looper (*Pseudoplusia includens*), forage looper (*Caenurgina erechtea*) and celery looper (*Anagrapha falcifera*); cabbageworms including the imported cabbageworm (*Pieris rapae*) and the European cabbageworm (*Pieries brassicae*); tomato pinworm (*Keiferia lycopersicella*); tomato hornworm (*Manduca quinquemaculata*); leafminers (*Liriomyza* spp.); cotton leafworm (*Alabama argillacea*); corn rootworm; garden webworm (*Achyra rantalis*); grape leaffolder (*Desmia funeralis*); melonworm (*Diaphania hyalinata*); pickleworm (*Diaphania nitidalis*); achemon sphinx (*Eumorpha achemon*); sweet potato hornworm (*Agrius cingulata*); whitelined sphinx (*Hyles lineata*); lygus bugs (*Lygus* spp.); chinch bugs including *Blissus leucopterus* and false chinch bugs; sow bugs; pill bugs; citrus rust mite; pill wood lice; wheat cockchafer; white grubs and cockchafers; *Hoplochelis marginalis* and *Melolontha melontha*; storage pests such as *Prostephanus truncatus* and *Sitophilus zeamais*; soil insects; and various other insect pests in the orders, Isopoda, Diplopoda, Chilopoda, Symphyla, Thysanura, Collembola, Orthoptera, Dermaptera, Anoplura, Mallophaga, Thysanoptera, Heteroptera, Homoptera, Lepidoptera, Coleoptera, Diptera, Siphonaptera, Thysaoptera, Acarina, Arachnida, etc. and the families Plutellidae, Acrididae, Tettigoniidae, Gryllidae, Cryllotalpidae, Pyralidae, Sphingidae, Noctuidae, Pyralidae, Xylophagidae, Scarabaeidae, Scolytidae, Platypodidae, Lymexylidae, Nitidulidae, Pseudococcidae, Aphidae, Dalphacidae, Cicadellidae, Cercopidae, Aleyodidae, Coccoidea, etc. It will be recognized that the insects listed above are representative examples of insects and arthropods which may be attracted and/or controlled according to the present invention, but such listing is not intended as a limitation to certain species as numerous other insect and arthropod species to which the invention may be applied will be apparent to those skilled in the art.

It will be noted from the discussion above and examples and results below that attractiveness, pathogenicity and virulency toward the targeted insect are dependent in some degree upon factors including choice of mycopesticidal species, host range and specificity, selection of a strain within that species and selection of substrate. Entomopathogenic fungi also vary greatly in host specificity. Some entomopathogenic fungi are highly specific, such as *Pandora neoaphidis*, which is restricted to aphids. Other entomopathogenic fungi have wide host ranges, such as *Beauveria bassiana*, which is known to infect over 700 species of arthropods. Other species with wide host ranges include *Metarhizium anisopliae, Paecilomyces farinosus* and *Zoophthora radicans*. However, in the laboratory, isolates of fungi with wide host ranges are generally most virulent to the host from which they were first isolated; certainly their host range is much more restricted than that of the species to which they belong. Goettel et al., "Safety to Nontarget Invertebrates of Fungal Biocontrol Agents," in: Laird et. al. (eds.) *Safety of Microbial Insecticides*, pp. 209-232 (1990). Furthermore, fungi with wide host ranges are frequently even more specific under field conditions. There are reports of fungi attacking only one host even though closely related host species are present. Discrepancies between reports of social insect host specificity may be related to a general difference between tropical vs. temperate habitats rather than to the specific fungi and social insect species involved. Schmid-Hempel, supra at p. 44. Such specificity is thought to be due to the complex biotic and abiotic interactions in the field. This indicates that it should be possible, using no more than routine experimentation and bioassays of mycopesticidal strains and of the appropriate orders, families, genera, species and varieties of targeted pest insects, to isolate and use strains and substrates wherein the desired characteristics are maximized with respect to either a targeted insect or targeted insect group, thereby producing a species-specific, genus-specific, family-specific or order-specific entomopathogenic host specific fungal strain. Such entomopathogenic strains selected for host range and specificity may be similarly selected for minimal or no infection, or virulence towards beneficial insects or non-targeted insects.

EXAMPLE 1

Attracting and Controlling Mosquitoes, Which Can Carry Viruses

Rice colonized by preconidial mycelium of *Metarhizium anisopliae* (ATCC #62716, and "F52") fungus clearly attracted *Aedes aegypti* females. Using an olfactometer in choices tests, the mycelium grown on rice attracted the female mosquitoes significantly over the controls. By comparison in the olfactometer, response of these host-seeking *Aedes aegypti* to a hand is about 83% to $CO_2$ (Allan et al. 2006). Combining the preconidial mycelium and the extracts from the same mycelium resulted in attractancy of mosquitoes to more than 80% equivalency to a human hand, far more so than the mycelium or extract alone. Since the actively growing mycelium is also outgassing carbon dioxide (but the extract does not), the added attractiveness of using an ethanolic/water extract is significant. *Aedes* mosquitoes spread viruses such as yellow fever, Chikungunya fever, and Dengue fever. Adding antiviral medicines previously proven useful, or yet to be discovered, to the extracts or mycelium of the preconidial entomopathogenic fungus, would abate the spread of disease, whether or not insect mortality occurred.

EXAMPLE 2

Attracting and Controlling Mosquitoes, Which Can Carry Malaria Protozoa

Prepare mycelium and extracts by the methods described herein. Mix in DDT, chemical pesticides, purified artemesinin or its crude, less expensive precursors, to the extracts and mycelium from preconidial entomopathogenic fungi such as *Metarhizium anisopliae* to bait and control stations, nets, or into standing water. Place these mixtures in environments where the mosquitoes exist, including *Anopheles gambiae* or any of its 30-40 species relatives, all of which carry Malaria protozoa (*Plasmodium falciparum*).

EXAMPLE 3

Attracting and Controlling Flies, Which Can Carry Viruses

Prepare the preconidial mycelium and extracts of the preconidial mycelium *Metarhizium anisopliae* according the methods described previously and blend with ribavirin, oseltamivir, and other antiviral drugs in pure or crude form to preconidial extracts and/or mycelium of *Metarhizium anisopliae* to attract house flies or blow ("blue bottle") flies and upon contact or ingestion, reduce the viral loads of flu viruses they carry, thus reducing their contagiousness.

EXAMPLE 4

Attracting and Controlling Flies, Which Can Carry Bacterial and Protozoa Pathogens Prepare the preconidial mycelium and extracts of the preconidial mycelium *Metarhizium anisopliae* according the methods described previously and blend with antimicrobial agents active against bacteria and protozoa. Use this blend to attract Tsetse fly carrying species of the protozoan genus *Trypanosoma* causing often-fatal "sleeping sickness." Use this blend to attract house flies (*Musca domestica*) and Blow Flies (Calliphoridae, *Calliphora vicina*, and related species), which carry the pathogens *Staphylococcus aureus*, *Streptococcus pyogenes*, *Bacillus anthracis*, *Listeria*, *Salmonella*, *Clostridium*, and *Enterococci*, which subsequent to contact, result in reduced pathogen payloads and infectivity.

EXAMPLE 5

Attracting and Controlling Ants, Which Can Carry Pathogenic Bacteria

Prepare the preconidial mycelium and extracts of the preconidial mycelium *Metarhizium anisopliae* according the methods described previously and blend with antimicrobial agents active against bacteria and protozoa. Use this blend to attract ants, such a Pharaoh ants and Fire Ants carrying pathogenic bacteria (*Salmonella*, *Staphylococcus*, *Streptococcus*, and *Clostridium*, etc.) resulting in reductions in their pathogens, making them less contagious and less infectious.

EXAMPLE 6

Attracting and Controlling *Cimex* Species (Bed Bugs), Which Carry Pathogenic Bacteria Prepare the preconidial mycelium and extracts of the preconidial mycelium *Metarhizium anisopliae* according the methods described previously and blend with antimicrobial agents active against *Staphylococcus aureus* bacteria. Use this blend to attract and control bed bugs resulting in reductions in their levels of *Staphylococcus aureus* bacteria, making them less contagious, reducing infectivity.

EXAMPLE 7

Attracting and Controlling Lice and Ticks, Which Carry Pathogenic Bacteria

Prepare the preconidial mycelium and extracts of the preconidial mycelium *Metarhizium anisopliae* according the methods described previously and blend with antimicrobial agents active against *Rickettsia* spp. (the cause of Rocky Mountain Spotted fever), *Bartonella vinsonii* and *B. henseiae* causing intramuscular infections, *Borrelia burgdorferi* causing Lyme disease. Use this blend to attract and control pathogen bearing lice and ticks, resulting in reductions in their levels of pathogenic bacteria, making them less contagious, reducing infectivity.

EXAMPLE 8

Attracting and Controlling Fleas, Which Carry Pathogenic Bacteria

Prepare the preconidial mycelium and extracts of the preconidial mycelium *Metarhizium anisopliae* according the methods described previously and blend with antimicrobial agents active against the bacteria *Yernsia pestis* causing bubonic plague. Use this blend to attract and control pathogen-bearing fleas, resulting in reductions in their levels of pathogenic bacteria, making them less contagious, reducing infectivity.

EXAMPLE 9

Attracting and Controlling Midges, Which Carry Pathogenic Viruses

Prepare the preconidial mycelium and extracts of the preconidial mycelium *Metarhizium anisopliae* according the methods described previously and blend with antiviral agents active against viruses (Blue tongue virus to cattle, epizootic hemorrhagic diseases). Use this blend to attract and control pathogen-bearing midges, resulting in reductions in their levels of pathogenic bacteria, making them less contagious, reducing infectivity.

EXAMPLE 10

Attracting and Controlling Flies Carrying Viruses

Prepare the preconidial mycelium and extracts of the preconidial mycelium *Metarhizium anisopliae* according the methods described previously and blend with extracts of polypore mushroom mycelium such as *Fomitopsis officinalis, Fomitopsis pinicola, Fomitporia robustus, Piptoporus betulinus, Trametes versicolor, Trametes elegans, Ganoderma lucidum, Ganoderma applanatum, Ganoderma annularis, Ganoderma oregonense, Ganoderma resinaceum, Ganoderma tsugae, Heterobasidion annosum, Inonotus obliquus, Antrodia camphorate, Rigidoporus ulmarius, Perenniporia fraxinophila, Psilocybe cyanescens, Psilocybe azurescens, Psilocybe cubensis* and other mushroom-derived antiviral drugs in pure or crude form to preconidial extracts and mycelium of *Metarhizium anisopliae* to attract house flies or Blow ("blue bottle") flies and upon contact, reduce the viral loads they carry, thus reducing their contagiousness.

EXAMPLE 11

Attract and Control Flies to Insect Control Devices

Add preconidial extracts and/or mycelium of *Metarhizium anisopliae* (prepared according the methods described previously, and blended with antimicrobial and antiviral agents) to insect trapping and killing contraptions used for limiting the spread of zoonotic disease such as 'bug zappers' (BASF's Vector™), forced airflow (fan) trapping systems, $CO_2$ emitters, laser target-and-kill systems, soaping systems, sticky mats, and bug nets, resulting in reducing the threat of the contagions flying insects carry.

EXAMPLE 12

Attracting and Controlling Disease-Bearing Insects with Cellulosic Materials

Add preconidial extracts and/or mycelium of *Metarhizium anisopliae* (prepared according the methods described previously, and blend with antimicrobial and antiviral agents) to fabric clothes, burlap sacks, wood chips, straw, to attract insects and arthropods carrying pathogens that results in a reduced pathogen load within these insects and arthropods subsequent to contact.

EXAMPLE 13

Attracting Mosquitoes to Attract Disease Carrying Bats and Birds

Prepare the preconidial mycelium and extracts of the preconidial mycelium *Metarhizium anisopliae* according the methods described previously and blend with antimicrobial and antiviral agents active against the contagions carried by disease carrying bats and birds. Use this blend to attract mosquitoes and other flying insects, which in turn will attract and control the movement of bats and birds. The ingestion of the insects, now carrying antimicrobial and antiviral agents, can then reduce the pathogen payload of the bats and birds, thereby reducing contagion risk.

EXAMPLE 14

Blending Antiviral Drugs with Extracts and Mycelium of Preconidial Entomopathogenic Fungi Blend the extracts or mycelia of preconidial entomopathogenic fungi with the less expensive antiviral drug precursors, expired antiviral drugs, or antiviral drugs such as Abacavir, Aciclovir, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Famciclovir, Fomivirsen, Fosamprenavir, Foscarnet, Fosfonet, Ganciclovir, Ibacitabine, Imunovir, Idoxuridine, Imiquimod, Indinavir, Inosine, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir (Tamiflu), Peginterferon alfa-2a, Penciclovir, Peramivir, Pleconaril, Podophyllotoxin, Protease inhibitors, Raltegravir, Reverse transcriptase inhibitor, Ribavirin, Rimantadine, Ritonavir, Pyramidine, Saquinavir, Stavudine, Tea tree oil, Tenofovir, Tenofovir disoproxil, Tipranavir, Trifluridine, Trizivir, Tromantadine, Truvada, Valaciclovir (Valtrex®), Valganciclovir, Vicriviroc, Vidarabine, Viramidine, Zalcitabine, Zanamivir (Relenza®) and Zidovudine to attract disease carrying insects and arthropods, and upon contact or ingestion, reduce their pathogenic payloads, thus reducing their contagiousness, and limiting disease transmission.

EXAMPLE 15

Blending Antibacterial Drugs with Extracts and Mycelium of Preconidial Entomopathogenic Fungi Blend the extracts or mycelia of preconidial entomopathogenic fungi with the less expensive antibacterial drug precursors, expired antibacterial drugs, or antibacterial drugs such as Amoxycillin, Ampicillin, Cipro, Duricef, Erythromycin, Floxin, Levaquin, Roxithromycin, Suprax, and Zithromax to attract disease carrying insects and arthropods, and upon contact or ingestion, reduce their pathogenic payloads, thus reducing their contagiousness, and limiting disease transmission.

EXAMPLE 16

Blending Antiviral Drugs with Extracts and Mycelium of Preconidial Entomopathogenic Fungi to Protect Plants From Viral Diseases Blend the extracts or mycelia of preconidial entomopathogenic fungi with antiviral drugs that protect plants to attract disease carrying insects and arthropods, and upon contact or ingestion, reduce their pathogenic payloads, thus reducing their contagiousness, and limiting disease transmission, thus protecting plants.

Leafhoppers, and white flies, which transmit viruses to plants, can be attracted to the extracts and mycelium of preconidial entomopathogenic fungi and limit viral disease transmission. Moreover, when antiviral drugs or their less pure, crude precursors are employed in combination with the extracts of preconidial entomopathogenic mycelium or with the preconidial mycelium of entomopathogenic fungi, the viral transmission threat from white flies and leaf hoppers is reduced or eliminated, thus saving crops from the damaging effects of viruses. Two exemplary examples are the beet leafhopper, *Circulifer tenellus* spreads curly top virus; *Macrosteles facsifrons* spreads mycoplasma to hundreds of plants, including many vegetables. Additionally, hundreds of species in family Cicadellidae transmit plant diseases, many of which are viruses.

EXAMPLE 17

Blending Extracts and Mycelium of Preconidial Entomopathogenic Fungi with Genetically Modified Gene Sequences Blend extracts of preconidial entomopathogenic mycelium or with the preconidial mycelium of entomopathogenic fungi to attract and control insects and arthropods that transmit contagions that harm plants, and which results in making contact with genetically modified gene sequences, further resulting in the protection of plants from viruses and other contagions carried by insects and arthropods.

EXAMPLE 18

Blending Extracts and Mycelium of Preconidial Entomopathogenic Fungi With Bacteriophages to Limit Disease Transmission Blend extracts of preconidial entomopathogenic mycelium or with the preconidial mycelium of entomopathogenic fungi to attract and control insects and arthropods that transmit contagions that harm plants and animals with bacteriophages, thus protecting plants and animals by the effect of the bacteriophages' ability to reduce or fend off transmittable diseases.

No limitations with respect to the specific embodiments and examples disclosed herein are intended or should be inferred, as the examples and embodiments are representative only. While examples and preferred embodiments of the present invention have been shown and described, it will be apparent to those skilled in the art, or ascertainable using no more than routine experimentation, that many changes and modifications may be made without departing from the invention in its broader aspects. The appended claims are therefore intended to cover all such changes, modifications and equivalents as fall within the true spirit and scope of the invention.

I claim:

1. A method comprising presenting an effective attracting amount of a preconidial preparation of an entomopathogenic fungus to attract and control arthropods that carry zoonotic diseases, wherein the preconidial preparation is selected from the group consisting of preconidial mycelium, extract of preconidial mycelium and both preconidial mycelium and extract of preconidial mycelium, wherein non-sporulating sectors are selectively cultured to produce the preconidial mycelium, wherein the preconidial mycelium contains less than 100 conidia per gram of myceliated substrate, wherein the preconidial preparation of an entomopathogenic fungus is blended with mushroom preparations selected from the group consisting of mycelium of *Fomitopsis officinalis, Fomitopsis pinicola, Fomitporia robustus, Piptoporus betulinus, Trametes versicolor, Trametes elegans, Ganoderma lucidum, Ganoderma applanatum, Ganoderma annularis, Ganoderma oregonense, Ganoderma resinaceum, Ganoderma tsugae, Heterobasidion annosum, Inonotus obliquus, Antrodia camphorate, Rigidoporus ulmarius, Perenniporia fraxinophila, Psilocybe cyanescens, Psilocybe azurescens* and *Psilocybe cubensis* mushrooms, extracts of the mycelium of said mushroom and combinations thereof, and wherein the arthropods are selected from the group consisting of insects, arachnids and myriapods.

2. The method of claim 1 wherein the insects are selected from the group consisting of malaria-carrying mosquitoes, virus-carrying mosquitoes, contagion-carrying flies, contagion-carrying ants, contagion-carrying bedbugs, contagion-carrying fleas and contagion-carrying midges and the arachnid is selected from the group consisting of virus-carrying ticks and contagion-carrying ticks.

3. The method of claim 1 wherein the entomopathogenic fungus is selected from the group consisting of the *Deuteromycetes Metarhizium, Beauveria, Paecilomyces, Hirsutella, Verticillium, Culicinomyces, Nomuraea* and *Aspergillus*, the Ascomycetes *Cordyceps, Ophiocordyceps* species and their anamorphs, Ascosphaera, Torrubiella, Hypocrella and its Aschersonia anamorph and combinations thereof.

4. The method of claim 1 wherein the entomopathogenic fungus is selected from the group consisting of *Metarhizium anisopliae, Metarhizium flaviridq Beauveria bassiana, Beauveria brongniartii, Paecilomyces farinosus, Paecilomyces fumosoroseus, Verticillium lecanii Hirsutella citriformis, Hirsutella thompsoni, Aschersonia aleyrodis, Entomophaga grylli, Entomophaga maimaiga, Entomophaga muscae, Entomophaga praaxibulli, Entomophthora plutellae, Zoophthora radicans, Neozygites floridana, Nomuraea rileyi, Pandora neoaphidis, Tolypocladium cylindrosporum, Culicinomyces clavosporus, Lagenidium giganteum, Cordyceps variabilis, Cordyceps facis, Cordyceps* (Ophiocordyceps) *subsessilis, Cordyceps myrmecophila, Cordyceps sphecocephala, Cordyceps entomorrhiza, Cordyceps gracilis, Cordyceps militaris, Cordyceps washingtonensis, Cordyceps melolanthae, Cordyceps ravenelii, Cordyceps unilateralis, Cordyceps sinensis, Cordyceps clavulata*, and combinations thereof.

5. The method of claim 1 wherein the entomopathogenic fungus is selected from the group consisting of *Cordyceps sinensis, Cordyceps subsessilis, Cordyceps militaris, Cordyceps unilateralis, Ophiocordyceps* species and their anamorphs including *Metarhizium, Beauveria, Paecilomyces, Hirsutella, Beauveria* and combinations thereof, wherein the insects are selected from the group consisting of mosquitoes, flies, bed bugs, fleas, midges and other insects and wherein the arthropods are selected from the group consisting of spiders, ticks and mites.

6. The method of claim 1 wherein the insects and the arthropods that carry zoonotic diseases are attracted to a locus for control.

* * * * *